(12) United States Patent
Kurata et al.

(10) Patent No.: US 6,531,642 B2
(45) Date of Patent: Mar. 11, 2003

(54) WATER-DECOMPOSABLE ABSORBENT ARTICLE FOR PANTYLINERS, SANITARY NAPKINS, INCONTINENCE PADS, DISPOSABLE DIAPERS AND THE LIKE

(75) Inventors: Nobuhiro Kurata, Kagawa (JP); Mitsuhiro Wada, Kagawa (JP); Megumi Tokumoto, Kagawa (JP)

(73) Assignee: Uni-Charm Corporation, Kinsei (JP)

(*) Notice: Subject to any disclaimer, the term of this patent is extended or adjusted under 35 U.S.C. 154(b) by 34 days.

(21) Appl. No.: 09/746,032

(22) Filed: Dec. 21, 2000

(65) Prior Publication Data

US 2001/0014795 A1 Aug. 16, 2001

(30) Foreign Application Priority Data

Jan. 6, 2000 (JP) ........................................ 2000-000575

(51) Int. Cl.[7] ................................................. A61F 13/15
(52) U.S. Cl. ........................ 604/364; 604/367; 604/387; 604/382; 604/385.01
(58) Field of Search .................................. 604/367, 387, 604/364, 382, 385.01, 370, 372

(56) References Cited

U.S. PATENT DOCUMENTS

| | | | | |
|---|---|---|---|---|
| 3,683,919 A | * | 8/1972 | Ells .............................. | 604/364 |
| 5,185,009 A | | 2/1993 | Sitnam ......................... | 604/364 |
| 5,300,358 A | * | 4/1994 | Evers ........................... | 428/422 |
| 5,722,966 A | * | 3/1998 | Christon et al. ............. | 604/364 |
| 5,769,833 A | * | 6/1998 | Hasse ........................... | 604/359 |
| 5,885,265 A | | 3/1999 | Osborn ......................... | 604/367 |

FOREIGN PATENT DOCUMENTS

| | | |
|---|---|---|
| EP | 0589437 A1 | 3/1994 |
| GB | 2295553 | 6/1996 |
| JP | 11-500341 | 1/1999 |
| WO | WO92/02199 | 2/1992 |

* cited by examiner

*Primary Examiner*—John J. Calvert
*Assistant Examiner*—Angela J. Grayson
(74) *Attorney, Agent, or Firm*—Darby & Darby

(57) ABSTRACT

Provided is a water-decomposable absorbent article including a water-decomposable back layer, a water-decomposable and liquid-pervious surface layer, and a water-decomposable absorbent layer sandwiched between the back layer and the surface layer and having a smaller planar dimension than the back layer and the surface layer. The absorbent article includes an inner region in which the absorbent layer is present, and an outer peripheral region having the back layer and the surface layer bonded to each other without interposing the absorbent layer therebetween and being formed in a predetermined width spaced from a peripheral edge of the absorbent article. A thermoplastic water-soluble adhesive is applied in a strip shape between the back layer and the surface layer in a predetermined width along the peripheral edge in the outer peripheral region. The back layer and the surface layer are heat-sealed with the thermoplastic water-soluble adhesive disposed therebetween in the outer peripheral region.

7 Claims, 2 Drawing Sheets

WATER-DECOMPOSABLE ABSORBENT ARTICLE FOR PANTYLINERS, SANITARY NAPKINS, INCONTINENCE PADS, DISPOSABLE DIAPERS AND THE LIKE

BACKGROUND OF THE INVENTION

1. Field of the Invention

The present invention relates to a water-decomposable absorbent article for pantiliners, sanitary napkins, incontinence pads, disposable diapers and the like.

2. Description of the Related Art

Recently, absorbent articles disposable in flush toilets have come available, including, for example, pantiliners, sanitary napkins, incontinence pads, disposable diapers and the like.

Such water-decomposable absorbent articles comprise a combination of materials easily decomposable in water, in which the water-decomposable materials are bonded to each other. If the water-decomposable materials are not bonded firmly to each other in some degree in them, the water-decomposable absorbent articles could not retain their shape during their use, arid will be loosened to lose their fittability to the skin of wearers or will be broken. However, if the constituent water-decomposable materials are bonded too firmly to each other, they could be hardly peeled from each other in flush toilets and septic tanks.

If the water-decomposable materials constituting such absorbent articles could not be immediately separated into the individual constituent layers in septic tanks, the absorbent articles could hardly sink therein owing to the air existing in their layers. When the water-decomposable materials are sunk in septic tanks to receive a large amount of water therein, they can be readily decomposed in water and biodegraded in microorganisms living in water. Therefore, if absorbent articles could not sink in septic tanks, they will be decomposed extremely slowly.

To that effect, water-decomposable absorbent articles are required to have two contradictory functions, one being the bonding strength to ensure shape retention during their use and the other being the rapid decomposability in water after discarded. To meet this requirement, for example, International Unexamined Patent Publication (Kohyo) No. Heisei 11-500341 discloses an absorbent article comprising a water-decomposable top sheet, a water-decomposable back sheet and a water-decomposable absorbent layer sandwiched between the two sheets, in which the constituent components are bonded to each other with a water-soluble adhesive disposed therebetween.

The absorbent article disclosed in this publication is so constituted that no absorbent layer exists in the peripheral region, and the top sheet and the back sheet are bonded to each other with a water-soluble hot-melt adhesive or a water-soluble emulsion adhesive disposed therebetween in the peripheral region.

However, in the absorbent article disclosed in International Unexamined Patent Publication (Kohyo) No. Heisei 11-500341, a water-soluble hot-melt adhesive is applied to the peripheral region to form a spiral adhesive pattern therein, or a water-soluble emulsion adhesive is applied thereto. In this, therefore, the adhesiveness between the top sheet and the back sheet in the peripheral region of the absorbent article is not satisfactory. In that condition, the top sheet and the back sheet are often peeled off from each other in the peripheral region while the absorbent article is used, and, as a result, the absorbent article could not retain its shape, and will be often loosened or broken during its use.

SUMMARY OF THE INVENTION

An object of the present invention is to provide a water-decomposable absorbent article in which the constituent components are more firmly bonded to each other in the peripheral region of the article to thereby enhance the shape retention of the article during its use, but could be readily separated from each other when disposed of in flush toilets.

According to one aspect of the invention, a water-decomposable absorbent article may comprise a water-decomposable back layer, a water-decomposable and liquid-pervious surface layer, and a water-decomposable absorbent layer sandwiched between the back layer and the surface layer and having a smaller planar dimension than the back layer and the surface layer, wherein;

the absorbent article including an inner region in which the absorbent layer is present, and an outer peripheral region having the back layer and the surface layer bonded to each other without interposing the absorbent layer therebetween and being formed in a predetermined width spaced from a peripheral edge of the absorbent article; a thermoplastic water-soluble adhesive is applied in a strip shape between the back layer and the surface layer in a predetermined width along the peripheral edge in the outer peripheral region; and the back layer and the surface layer are heat-sealed with the thermoplastic water-soluble adhesive disposed therebetween in the outer peripheral region.

For example, the thermoplastic water-soluble adhesive is polyvinyl alcohol (PVA), more preferably a cold water-soluble polyvinyl alcohol derivative.

In the invention, the outer peripheral region of the absorbent article is heat-sealed with a thermoplastic water-soluble adhesive, for example, with PVA, disposed in a predetermined width of the outer peripheral region. Therefore, the shape retention of the absorbent article during its use is good. The bonding between the layers in the region ensures high adhesiveness in dry. During its use, the absorbent article mainly receives body fluid in an inner region, and the body fluid absorbed by it hardly spreads to the outer peripheral region. Therefore, the surface layer and the back layer are hardly peeled off from each other in the outer peripheral region, so that the shape of the absorbent article can be easily retained during its use.

When the absorbent article is, after used, disposed of in flush toilets, the water-soluble adhesive such as PVA, swells and dissociates in water, and the back layer and the surface layer are peeled off from each other. As a result, the constituent layers of the thus-disposed absorbent article are separated from each other and are readily decomposed in septic tanks, etc.

In particular, in the outer peripheral region of the absorbent article, no absorbent layer is sandwiched between the back layer and the surface layer, and the back layer and the surface layer are directly bonded to each other with the water-soluble adhesive disposed therebetween. Accordingly, the absorbent article is well self-retainable as a whole, and after it is disposed of, the back layer and the surface layer constituting it are readily peeled off from each other and all the constituent layers are therefore readily separated from each other.

Preferably, in the absorbent article of the invention, a layer of the thermoplastic water-soluble adhesive is formed almost entirely both in the outer peripheral region of the article and in the inner region thereof inside the outer peripheral region. For example, the thermoplastic water-soluble adhesive layer is made of an independent film disposed separately from the back layer. Preferably, the film for the thermoplastic water-soluble adhesive layer is laminated on the back layer.

In case where the thermoplastic water-soluble adhesive layer is disposed almost entirely on the back layer with the absorbent layer overlying the back layer in the preferred manner as above, the thermoplastic water-soluble adhesive layer can prevent liquid permeation through it and therefore can prevent body fluid from passing outside through the back layer.

According to another aspect of the invention, a water-decomposable absorbent article may comprise a water-decomposable back layer, a water-decomposable and liquid-pervious surface layer, and a water-decomposable absorbent layer sandwiched between the back layer and the surface layer and having a smaller planar dimension than the back layer and the surface layer, wherein;

the absorbent article including an outer peripheral region having the back layer and the surface layer bonded to each other without interposing the absorbent layer therebetween and being formed in a predetermined width spaced from a peripheral edge of the absorbent article; the back layer and the surface layer in the outer peripheral region are bonded to each other by bonding means adapted for being dissociated in water; and the bonding means is at least partially omitted to form an omitted portion.

In this aspect of the invention, the bonding means in the outer peripheral region of the absorbent article can enhance the shape retention of the article during its use, and when the absorbent article is, after used, disposed of in flush toilets, a large amount of water penetrates into the inside area of the article through the omitted portion of the bonding means, thereby facilitating the dissociation of the bonding means as triggered at the omitted portion. In addition, the water having penetrated into the inside area of the absorbent article through the omitted portion acts to remove air away from the absorbent article, and, as a result, the absorbent article thus containing water can readily sink in septic tanks and can be readily decomposed therein.

In particular, it is desirable that the omitted portion is provided at least one end edge in the longitudinal direction of the absorbent article.

No omitted portion is provided at both side edges in the transverse direction of the absorbent article. Therefore, while used, the absorbent article is free from the drawback of layer separation such that the surface layer and the back layer constituting it are peeled off from each other on both side edges in the transverse direction thereof owing to the movement of the body to which it is fitted.

For example, the bonding means is formed by heat-sealing the back layer and the surface layer with a thermoplastic water-soluble adhesive disposed therebetween.

The bonding means is partially omitted, and therefore immediately loses its bonding force when it receives a large amount of water, as triggered at the omitted portion. The absorbent article thus having lost its bonding force can sink in septic tanks and can be readily biodegraded. Therefore, the material for the bonding means in the absorbent article is not limited to only water-soluble adhesives such as PVA and others. As the case may be, the back layer and the surface layer constituting the absorbent article may be bonded to each other, for example, through mechanical compression sealing, or chemical hydrogen bonding, etc.

The absorbent article of the invention can retain its shape even when an adhesive is not provided between the surface layer and the absorbent layer and between the back layer and the absorbent layer in the inner region except for the outer peripheral region. However, so far as it does not detract from the decomposability of the absorbent article in water, the water-soluble adhesive may be provided between the surface layer and the absorbent layer and/or between the back layer and the absorbent layer to bond them in the inner region of the absorbent article.

DESCRIPTION OF THE PREFERRED EMBODIMENTS

Figure 1:
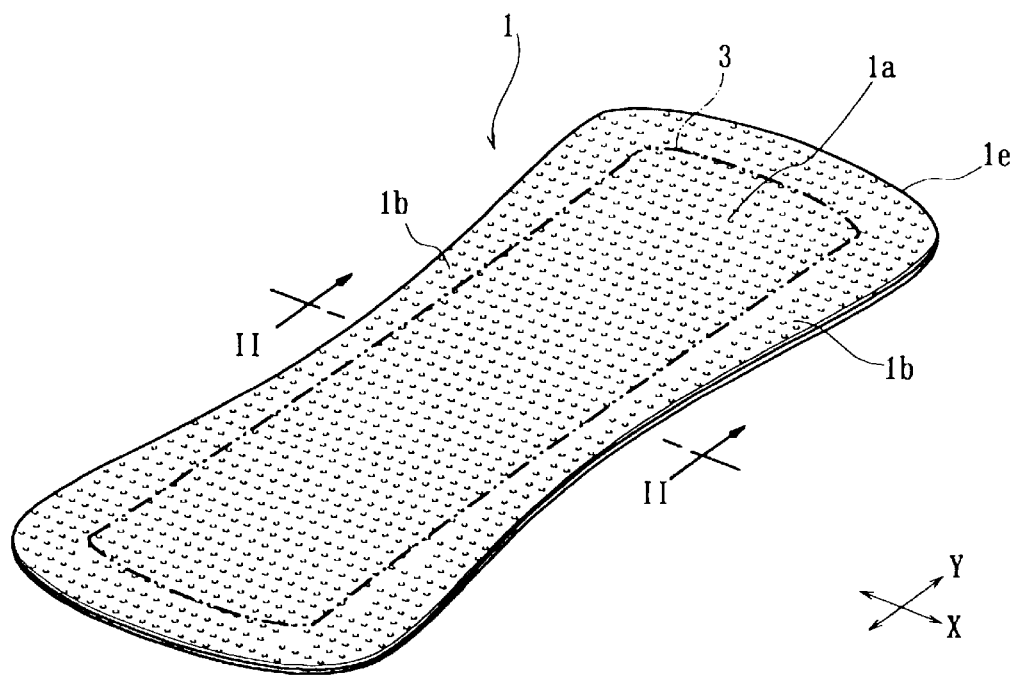
FIG. 1 is a perspective view of one embodiment of an absorbent article of the invention.
Figure 2:
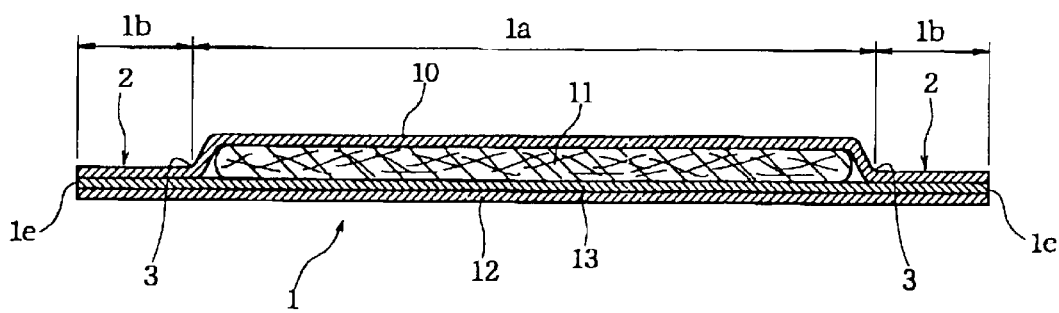
FIG. 2 is a cross-sectional view of the absorbent article of FIG. 1, cut along the line II—II.
Figure 3:
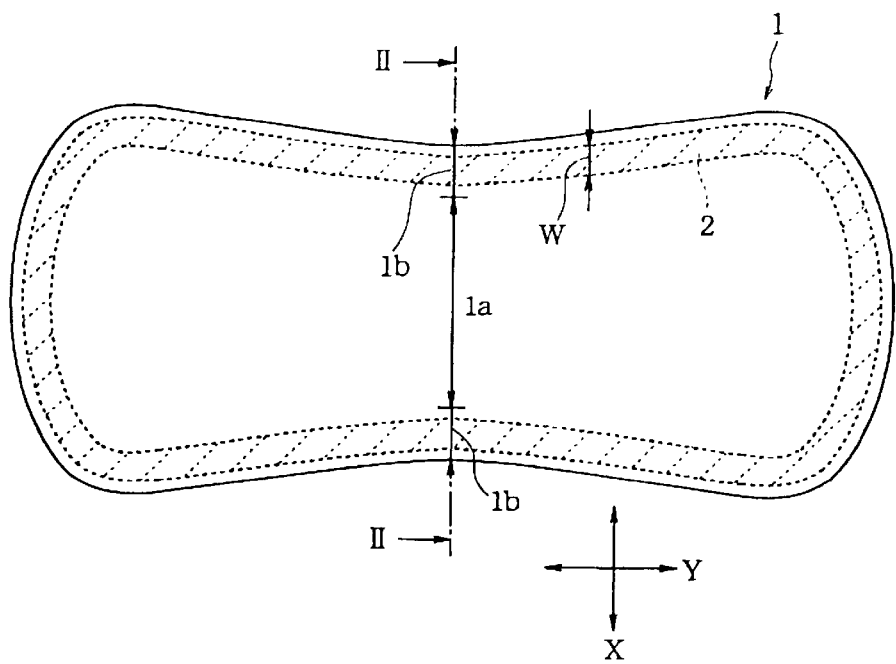
FIG. 3 is a plan view of the absorbent article as shown in FIG. 1 and FIG. 2.
Figure 4:
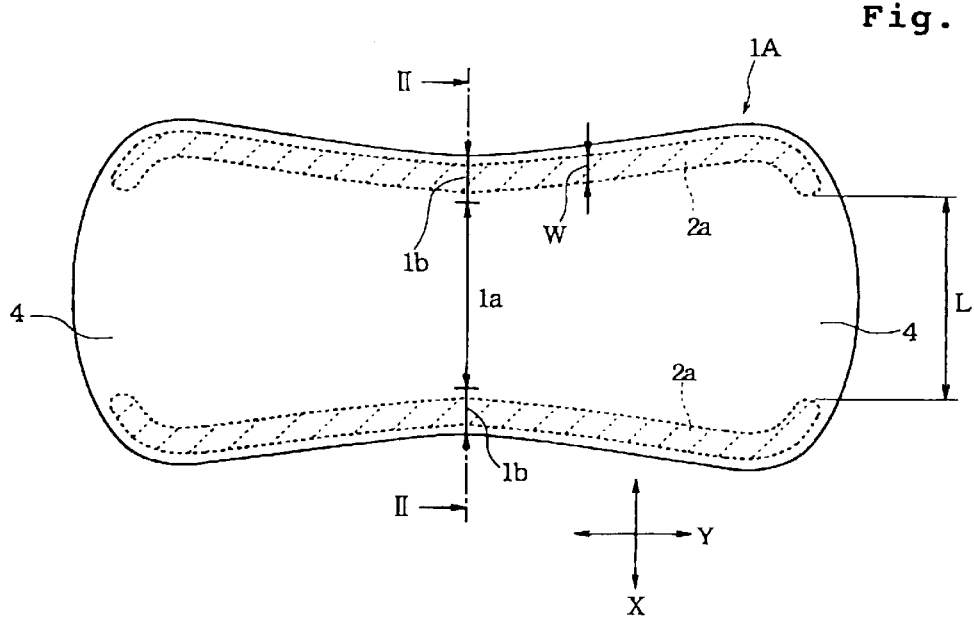
FIG. 4 is a plan view of another embodiment of the absorbent article of the invention.

The invention is described concretely with reference to the accompanying drawings. FIG. 1 is a perspective view of one embodiment of an absorbent article of the invention, looking from its top surface (this top surface serves as a body facing surface); FIG. 2 is a cross-sectional view of the absorbent article of FIG. 1, cut along the line II—II; and FIG. 3 and FIG. 4 are both plan views of different types of the absorbent articles of the invention, indicating the bonding profile of a round-seal portion formed in the article. In these drawings, a longitudinal direction of the absorbent article is designated by Y, and a transverse direction generally perpendicular to the direction Y is designated by X.

The absorbent article of the invention shown in FIG. 1 and FIG. 2 is for pantiliners or sanitary napkins. As shown in FIG. 2, an absorbent article 1 comprises a water-decomposable and liquid-pervious surface layer 10 which serves as a body facing surface, a water-decomposable back layer 12, and a water-decomposable absorbent layer 11 sandwiched between the surface layer 10 and the back layer 12. A thermoplastic water-soluble adhesive layer 13 is disposed between the back layer 12 and the absorbent layer 11.

The thermoplastic water-soluble adhesive layer 13 is of a water-soluble PVA, but preferably a cold water-soluble PVA derivative. This is provided almost entirely on the back layer 12. The water-soluble adhesive layer 13 is in the form of an independent film provided separately from the back layer 12, or is in the form of a film laminated on the back layer 12, or is coated almost entirely on the back layer 12.

In an outer peripheral region 1b of the absorbent article 1 that extends in a predetermined width from a peripheral edge 1e to a boundary 3 thereof, the surface layer 10 and the back layer 12 are laminated. Specifically, the planar dimension of the absorbent layer 11 is smaller than that of both the surface layer 10 and the back layer 12, and the absorbent layer 11 is present only in an inner region 1a existing inside the boundary 3.

In the outer peripheral region 1b, the surface layer 10 and the back layer 12 are heated under pressure so as to surround the absorbent layer 11. Concretely, without disposing the absorbent layer 11 therebetween, the surface layer 10 and the back layer 12 are heat-sealed with the thermoplastic water-soluble adhesive layer 13 of PVA or the like disposed between them, to thereby form a round-seal portion 2.

The width of the outer peripheral region 1b that extends from the peripheral edge 1e to the boundary 3 (the boundary 3 generally corresponds to the edge of the absorbent layer 11) preferably falls between 2 and 25 mm, more preferably between 8 and 20 mm.

The round-seal portion 2 may be formed to cover the entire width of the outer peripheral region 1b, or, as the case may be, the width W of the round-seal portion 2 in the outer peripheral region 1b may be smaller than the width of the outer peripheral region 1b, as shown in FIG. 3. In the embodiment illustrated in FIG. 3, the round-seal portion 2 is formed into a strip configuration to extend the entire periphery of the absorbent article, having a width designated by W. The width W of the round-seal portion 2 may fall, for example, between 1 and 4 mm or so.

If the width W is smaller than the lowermost limit of the defined range, the shape-retaining force of the absorbent article 1 will be low. However, if the width W is larger than the uppermost limit, the area of the absorbent layer in the inner region 1a shall decrease, so that the ability of the absorbent article 1 to absorb body fluid will be lowered. In addition, the absorbent article 1 having such a broad round-seal portion 2 will be poorly flexible and will give a hard feel to the skin of a wearer to which it is fitted.

In the illustrated absorbent article 1, a strip-like round-seal portion 2 having a predetermined width W is formed in the outer peripheral region 1b. With that, the surface layer 10 and the back layer 12 are surely bonded to each other in the outer peripheral region 1b. In addition, since the two layers 10 and 12 are heat-sealed in the strip-like region having such a predetermined width W, along with the thermoplastic water-soluble adhesive layer 13 of PVA or the like disposed therebetween, the bonding strength between the surface layer 10 and the back layer 12 is enhanced. Therefore, while the absorbent article 1 is fitted to the skin of a wearer, it surely retains its shape, and, in addition, the surface layer 10 and the back layer 12 constituting it are hardly peeled off from each other in the outer peripheral region 1b. Accordingly, during its use, the absorbent article 1 is hardly loosened or broken.

Since the heat-sealing in the outer peripheral region 1b is attained via the water-soluble adhesive layer 13 of PVA or the like disposed between the two layers 10 and 12, the water-soluble adhesive layer 13 well swells in water and loses its adhesiveness when the absorbent article 1 is, after used, disposed of in flush toilets and led to septic tanks. In the thus-discarded absorbent article 1, the surface layer 10 and the back layer 12 immediately peel off from each other in the outer peripheral region 1b.

As a result, the discarded absorbent article 1 is, when led to septic tanks and kept therein, readily separated into the surface layer 10, the back layer 12 and the absorbent layer 11. In addition, water penetrates into the inside area of the absorbent article 1 through the delaminated space in the outer peripheral region 1b, and acts to remove air away from the absorbent article 1. Accordingly, the absorbent article 1 thus containing water with little air therein can readily sink in septic tanks and is further separated into the individual layers and biodegraded therein.

In the invention, the surface layer 10 and the back layer 12 are bonded to each other via the thermoplastic water-soluble adhesive layer 13 therebetween, only in the outer peripheral region 1b of the absorbent article 1, so that the absorbent article 1 can retain its shape owing to the layer-to-layer bonding only in that region. Therefore, in the absorbent article 1, it is unnecessary to bond the constituent layers with an adhesive in the inner region 1a, and it is rather desirable not to bond them in the inner region 1a. When the absorbent article 1 is, after used, disposed of in flush toilets and led to septic tanks, the surface layer 10 and the back layer 12 constituting it are readily peeled off from each other in the round-seal portion 2 of the outer peripheral region 1b, and the absorbent article 1 is readily separated into the individual surface layer 10, back layer 12 and absorbent layer 11, and then immediately decomposed in water and biodegraded. If desired, however, the constituent layers may be partially bonded to each other with a rapidly water-soluble adhesive in the interface between the surface layer 10 and the absorbent layer 11 and/or the interface between the absorbent layer 11 and the back layer 12 in the inner region 1a of the absorbent article 1.

In the absorbent article 1, the water-soluble adhesive layer 13 is formed almost entirely on the top surface of the back layer 12, and it acts as a body fluid leak-preventing layer. In this, the body fluid having passed through the absorbent layer 11 is absorbed by the water-soluble adhesive layer 13 to prevent the body fluid from passing outside through the back layer 12.

As set forth above, the thermoplastic water-soluble adhesive layer 13 is preferably made of a water-soluble PVA film, more preferably a film of a cold water-soluble PVA derivative. The film prepared separately from the back layer 12 is laid over the back layer 12, or is integrated with the back layer 12 by means of lamination.

On the other hand, a thermoplastic water-soluble adhesive may be applied to the top surface of the back layer 12 to cover almost the entire area thereof. Except for PVA, any other water-soluble adhesives for heat-sealing are usable herein, including, for example, water-soluble polymers such as polyvinyl pyrrolidone, and isobutylene-maleic anhydride copolymer, etc.

The amount of the film-like water-soluble adhesive or the coating water-soluble adhesive applied to the round-seal portion 2 preferably falls between 10 and 30 $g/m^2$. Within the defined range, the adhesive does not interfere with smooth delamination in the round-seal portion 2 in the outer peripheral region 1b of the absorbent article disposed of in flush toilets and led to septic tanks, and its adhesiveness is enough for shape retention of the absorbent article 1 during its use.

The back layer 12 is readily dispersed in water jets in flush toilets or in water in septic tanks. It may be formed of water-decomposable paper, water-decomposable non-woven fabric or the like that contains water-dispersible fibers. For example, it may be made of (1) a water-decomposable paper sheet of pulp fibers in which the pulp fibers are bonded to each other via hydrogen bonding therebetween, (2) a water-decomposable paper sheet of pulp fibers and other water-dispersible fibers of rayon or the like in which the constituent fibers are bonded to each other with a water-soluble binder, (3) a water-decomposable paper sheet of water-decomposable fibers in which the constituent fibers are simply entangled, or (4) a water-decomposable non-woven fabric of water-dispersible fibers having a relatively short length where the constituent fibers are forcedly entangled through water-jetting treatment. If desired, the outer surface of the back layer 12 (this outer surface serves as a garment facing surface) may be coated with a water-soluble resin such as a polyvinyl alcohol, an unsaturated carboxylic acid copolymer or the like. Thus coated, the back layer 12 will be impervious to fluid.

The absorbent layer 11 may be made of, for example, water-decomposable paper, pulp or non-woven fabric. For example, air-laid pulp or the like may be formed into the absorbent layer 11 to have a unit weight (Metsuke) of from 50 to 70 g/m$^2$ or so. In case where water-decomposable paper is used for forming the absorbent layer 11, it is desirable that a plurality of relatively thin sheets of water-decomposable papers are stacked to form it, since the thus stacked sheets are well decomposable in water. For example, 4 to 8 sheets of water-decomposable paper having a unit weight of from 10 to 20 g/m$^2$ are stacked to form the absorbent layer 11. Sheets of water-decomposable paper coated with a water-swellable resin such as polyvinyl alcohol or the like may be stacked to form the absorbent layer 11.

The surface layer 10 is, for example, made of a water-decomposable non-woven fabric of spun lace. On the other hand, a plurality of sheets of water-decomposable paper may be stacked on a water-decomposable non-woven fabric to form the surface layer 10. In this case, the non-woven fabric and the water-decomposable paper may be integrated through hydrogen bonding or needling. Since the surface layer 10 acts to lead excretions to the underlying absorbent layer 11, it is preferably perforated to have a plurality of perforations through the entire area thereof, for example, as in FIG. 1.

FIG. 4 illustrates the second embodiment of the present invention.

In an absorbent article 1A as shown in FIG. 4, the materials of the constituent layers and the water-soluble adhesive layer 13 are the same as those in the absorbent article 1 illustrated in FIGS. 1, 2 and 3. In the outer peripheral region 1b, without disposing the absorbent layer 11 therebetween, the surface layer 10 and the back layer 12 are heat-sealed via the thermoplastic water-soluble adhesive layer 13 of, for example, a PVA film or the like disposed therebetween, thereby forming two round-seal portions 2a, 2a.

The round-seal portions 2a, 2a are the same as the round-seal portion 2 in the embodiment illustrated in FIGS. 1 to 3, in that they are formed into a strip configuration to have a predetermined width W. However, in the absorbent article 1A of FIG. 4, the round-seal portions 2a, 2a are formed at both side edges of the absorbent article 1A lying opposite one another in the transverse direction (in the X direction), and extending along each side edge in the longitudinal direction (in the Y direction). In this, the round-seal portions 2a, 2a are not endless, and are provided with an omitted portion 4 at least one end edge of the absorbent article 1A lying opposite one another in the longitudinal direction (in the Y direction). The embodiment illustrated in FIG. 4 has two omitted portions 4 at both end edges in the longitudinal direction, which, however, is not limitative. If desired, the omitted portion may be formed only at one end edge in the longitudinal direction, but not at the other end edge, on which, therefore, the round-seal portion is continuous.

The omitted portions 4 may be provided at both side edges of the absorbent article 1A lying opposite one another in the transverse direction (in the X direction), and extending along each side edge in the longitudinal direction (in the Y direction). However, in case where they are so provided at both side edges in the transverse direction X, the bonding strength between the surface layer 10 and the back layer 12 in the omitted portions become unsatisfactory relative to the shear force in the direction X of the absorbent article fitted to the skin of a wearer. Therefore, it is desirable that the omitted portions 4 are provided at the end edges in the longitudinal direction of the absorbent article, as shown in FIG. 4.

The absorbent article 1A is so constituted as to have the strip-like round-seal portions 2a, 2a formed on both side edges in the transverse direction to have a predetermined width W, and in this, the surface layer 10 and the back layer 12 are heat-sealed in the round-seal portions 2a, 2a. Therefore, while the absorbent article 1A is fitted to the skin of a wearer, it can well retain its shape, and is not loosened or broken by the shear force in the direction X. When the absorbent article 1A is, after used, disposed of in flush toilets, a large amount of water penetrates into it through the omitted portions 4, thereby facilitating the dissociation of the water-soluble adhesive layer 13 in the round-seal portions 2a, 2a as triggered at the omitted portions 4 to readily separate the article into individual layers.

In particular, since the water having penetrated into the inside area of the absorbent article through the omitted portion acts to move air away from the absorbent article, and, as a result, the absorbent article thus containing water can readily sink in septic tanks. Accordingly, even if the solubility in water of the round-seal portions 2a, 2a is poor, the absorbent article of this embodiment can well sink in septic tanks to receive a large amount of water therein, thereby being readily decomposed in water. In addition, even when the surface layer 10 and the absorbent layer 11, and/or the absorbent layer 11 and the back layer 12 are bonded to each other with the water-soluble adhesive therebetween in the inner region 1a, the absorbent article having sunk in septic tanks well receives a large amount of water through the omitted portions 4 and is readily separated into individual layers so that the surface layer 10 can be readily separated from the absorbent layer 11 and the absorbent layer 11 from the surface layer 12.

In order to ensure the penetration of a large amount of water into the absorbent article through the omitted portions 4, it is desirable that the omitted portions 4 have a width L of from 10 to 40 mm. If desired, the omitted portions 4 may be divided into plural parts on both end edges in the longitudinal direction thereof. In this case, the overall width of the plural parts to form one omitted portion at one end edge may fall within the defined range of the width L.

In that manner, the embodiment of FIG. 4 is so constituted that water is positively led into the inside area of the absorbent article 1A through the omitted portions 4. In this, therefore, even when the solubility in water of the round-seal portions 2a, 2a is relatively poor as set forth above, decomposition of the round-seal portions 2a, 2a can be well promoted as triggered at the omitted portion 4. Due to these omitted portions, the mode of forming the round-seal portions 2a, 2a is not limited to only heat-sealing with a thermoplastic water-soluble adhesive of PVA or the like. For this, therefore, employable is any other bonding means that includes, for example, bonding with any other water-soluble or water-swellable adhesives, hydrogen bonding, mechanical bonding, etc.

Preferably, in the invention, the back side of the absorbent article, that is, the outer surface of the back layer 12 (this outer surface serves as a garment facing surface) is entirely coated with an adhesive and further covered with a release film for protecting the adhesiveness of the adhesive while the absorbent article is not used. Also preferably, the release film is decomposable in water. Still preferably, the package for the absorbent article is also decomposable in water.

EXAMPLES

The invention is described in more detail with reference to the following Examples, which, however, are not intended to restrict the scope of the invention.

For the examples of the invention, pantiliners were prepared as shown in FIGS. 3 and 4. The pantiliner had a length of 140 mm and a width of 55 mm. For this, the surface layer 10 was made of a non-woven fabric of wet-spun lace having a unit weight (Metsuke) of 45 g/m$^2$, and the absorbent layer 11 was made by laminating five sheets of tissue papers (water-decomposable papers) having a unit weight (Metsuke) of 14 g/m$^2$.

In Example 1, used was a non-woven fabric of wet-spun lace having a unit weight of 45 g/m$^2$ for the back layer 12, and a water-soluble PVA film (having a unit weight of 40 g/m$^2$) was prepared for the water-soluble adhesive layer 13, separately from the back layer 12.

In Examples 2 and 3, used was the non-woven fabric of wet-spun lace having a unit weight of 45 g/m$^2$ for the back layer 12, and a water-soluble PVA film (having a unit weight of 30 g/m$^2$) serving as the water-soluble adhesive layer 13 was integrated with the back layer 12 by laminating them.

In Examples 1 and 2, the round-seal portion was formed entirely in the periphery of the pantiliner, as shown in FIG. 3. On the other hand, in Example 3, the round-seal portion was formed to have the omitted portions 4 on both end edges in the longitudinal direction of the pantiliner, as shown in FIG. 4. Each omitted portion 4 had a width L of 20 mm.

The round-seal portion 2 having a width W of 2 mm was formed by heat-sealing the surface layer 10 and the back layer 12 offset inwardly from the peripheral edge 1e of the pantiliner by 3 mm. The heat-sealing was effected at 120° C. under 3922 kPa for 3 seconds.

In Comparative Example 1, the constituent layers were the same as those in the Examples except that the water-soluble adhesive layer 13 was not provided, and the layers were heat-sealed in the outer peripheral region 1b under the same condition as in Examples.

In the respective Examples and Comparative Example, by means of the water-soluble adhesive layer 13, the surface layer 10 was not bonded to the absorbent layer 11 and the absorbent layer 11 was not bonded to the back layer 12, in the inner region 1a of the pantiliner.

All in the Examples and Comparative Example, the surface layer 10 was not bonded to the absorbent layer 11 and the absorbent layer 11 was not to the back layer 12, in the inner region 1a of the pantiliner.

The pantiliners thus produced in the Examples and Comparative-Example were subjected to a wear test, a test in a septic tank, and a test for decomposition in water. The data obtained are given in Table 1 below.

(Wear Test)

The samples were tested by ten panelists. After used, the condition of each sample was macroscopically checked. In Table 1, "○" indicates that the tested samples were not broken; and "x" indicates the tested samples were broken.

(Test in Septic Tank)

The samples were disposed of in a flush toilet and led to a septic tank. In the septic tank, the behavior of each sample was macroscopically checked. In Table 1, "○" indicates that the sample were pulverized into individual layers immediately when led into the septic tank; and "x" indicates that the samples were not separated into individual layers.

(Test for Decomposition in Water)

The samples were tested according to the water-decomposability test in JIS P-4501. Precisely, each sample was cut to have a length of 10 cm and a width of 10 cm, put into a 300 ml beaker filled with 300 ml of ion-exchanged water, and stirred therein with a stirrer. The revolution of the stirrer was 600 rpm. While stirred, the sample was periodically checked, and the time taken by it until its dispersion in water was recorded. In Table 1, "○" indicates that the samples were decomposed in water within 100 seconds; and "x" indicates that the samples were not decomposed in water.

TABLE 1

|  | Example 1 | Example 2 | Example 3 | Comparative Example 1 |
|---|---|---|---|---|
| (Constitution) |  |  |  |  |
| Surface Layer | wet-spun lace | wet-spun lace | wet-spun lace | wet-spun lace |
| Absorbent Layer | water-decomposable paper | water-decomposable paper | water-decomposable paper | water-decomposable paper |
| Adhesive Layer | PVA film |  |  |  |
| Back Layer | wet-spun lace | laminate of wet-spun lace and PVA film | laminate of wet-spun lace and PVA film | wet-spun lace |
| Wear Test | ○ | ○ | ○ | x (broken) |
| Test in Septic Tank | ○ | ○ | ○ | x (floating) |
| Test for Decomposition in Water | ○ | ○ | ○ | ○ |

As set forth above, the water-decomposable absorbent article of the invention has no absorbent layer in the outer peripheral region, and the surface layer and the back layer constituting it are heat-sealed with a water-soluble adhesive layer disposed therebetween, in the outer peripheral region. Therefore, since the surface layer and the back layer constituting it are firmly bonded to each other in the outer peripheral region, the absorbent article well retains its shape during its use. Furthermore, when the absorbent article is, after used, disposed of in flush toilets, it receives a large amount of water therein, and the surface layer and the back layer constituting it are separated from each other in the outer peripheral region, thereby facilitating rapid decomposition of the article within a short period of time.

While the invention has been described in detail and with reference to specific embodiments thereof, it will be apparent to one skilled in the art that various changes and modifications can be made therein without departing from the spirit and scope thereof.

Here, 'comprises/comprising' when used in this specification is taken to specify the presence of stated features, integers, steps or components but does not preclude the presence or addition of one or more other features, integers, steps, components or groups thereof.

What is claimed is:

1. A water-decomposable absorbent article comprising:
   a back layer made of laminate material of a water-decomposable sheet and a layer of thermoplastic water-soluble adhesive,
   a water-decomposable and liquid-pervious surface layer,
   a water-decomposable absorbent layer sandwiched between the back layer and the surface layer and having a smaller planar dimension than the back layer and the surface layer,
   the absorbent article including an outer peripheral region having the back layer and the surface layer bonded to each other without interposing the absorbent layer therebetween, and being formed in a predetermined width spaced from a peripheral edge of the absorbent article; and
   the back layer and the surface layer being heat-sealed by way of interposing the layer of thermoplastic water-soluble adhesive disposed therebetween along an entire length of the outer peripheral region.

2. The water-decomposable absorbent article as set forth in claim 1, wherein the thermoplastic water-soluble adhesive is polyvinyl alcohol.

3. The water-decomposable absorbent article as set forth in claim 1, wherein a layer of the thermoplastic water-soluble adhesive is formed almost entirely both in the outer peripheral region and in the inner region inside the outer peripheral region of the aborbent article.

4. The water-decomposable absorbent article as set forth in claim 3, wherein the thermoplastic water-soluble adhesive layer is made of an independent film disposed separately from the back layer.

5. The water-decomposable absorbent article as set forth in claim 3, wherein a film for the thermoplastic water-soluble adhesive layer is laminated on the back layer.

6. A water-decomposable absorbent article comprising:
   a back layer made of laminate material of a water-decomposable sheet and a PVA film;
   a water-decomposable and liquid-pervious surface layer;
   a water-decomposable absorbent layer sandwiched between the back layer and the surface layer and having a smaller planar dimension than the back layer and the surface layer;
   the absorbent article including an outer peripheral region having the back layer and the surface layer bonded to each other without interposing the absorbent layer therebetween, and being formed in a predetermined width spaced from a peripheral edge of the absorbent article, and
   the back layer and the surface layer being heat-sealed with interposing the PVA film therebetween along an entire length of the outer peripheral region.

7. A water-decomposable pantiliner comprising:
   a back layer made of laminate material of a water-decomposable sheet and aPVA film;
   a water-decomposable and liquid-pervious surface layer;
   a water-decomposable absorbent layer sandwiched between the back layer and the surface layer and having a smaller planar dimension than the back layer and the surface layer;
   the pantiliner including an outer peripheral region having the back layer and the surface layer bonded to each other without interposing the absorbent layer therebetween, and being formed in a predetermined width spaced from a peripheral edge of the pantiliner, and
   the back layer and the surface layer being heat-sealed with interposing the PVA film therebetween along an entire length of the outer peripheral region.

* * * * *